United States Patent [19]

Shoffner

[11] 4,174,351

[45] Nov. 13, 1979

[54] SEPARATION OF DISSIMILAR AMINES

[75] Inventor: James P. Shoffner, Elk Grove Village, Ill.

[73] Assignee: UOP Inc., Des Plaines, Ill.

[21] Appl. No.: 937,616

[22] Filed: Aug. 28, 1978

[51] Int. Cl.$^2$ .................. C07C 85/26; C07C 89/04
[52] U.S. Cl. .................. 260/582; 260/563 R; 260/563 C; 260/563 P; 260/570.5 R; 260/570.8 R; 260/570.9; 260/575; 260/583 N; 260/701
[58] Field of Search .............. 260/583 N, 582, 563 R, 260/563 C, 570.9, 570.8 R

[56] References Cited

U.S. PATENT DOCUMENTS

| | | | |
|---|---|---|---|
| 2,165,165 | 7/1939 | Dreisbach et al. | 260/582 |
| 2,671,110 | 3/1954 | Zbornik et al. | 260/582 |
| 2,946,822 | 7/1960 | Schenck et al. | 260/582 |
| 3,131,221 | 4/1964 | Remes et al. | 260/583 N |
| 3,149,162 | 9/1964 | Gardner et al. | 260/582 |
| 3,248,427 | 4/1966 | Greenfield | 260/582 X |
| 3,960,963 | 6/1976 | Gavin | 260/582 |

FOREIGN PATENT DOCUMENTS

| | | | |
|---|---|---|---|
| 355018 | 8/1931 | United Kingdom | 260/582 |
| 966812 | 8/1964 | United Kingdom | 260/582 |

OTHER PUBLICATIONS

Nagy et al., "Chem. Ab.", vol. 69, No. 43199p; (1968), No. 43200g.

Primary Examiner—Winston A. Douglas
Assistant Examiner—John Doll
Attorney, Agent, or Firm—James R. Hoatson, Jr.; Raymond H. Nelson; William H. Page, II

[57] ABSTRACT

Amines which are dissimilar in nature by virtue of possessing different substituents, different structures or position isomers may be selectively separated by treatment with a reactive carbonyl compound and an acid. The separation may be effected at reaction conditions which include a temperature in the range of from about ambient to about 150° C. and a pressure in the range of from about atmospheric to about 100 atmospheres. An example of this separation is the treatment of a mixture of m-toluidine and p-toluidine with benzaldehyde and trifluoroacetic acid. The m-toluidine will form an imine while the p-toluidine will form an acid salt.

10 Claims, No Drawings

SEPARATION OF DISSIMILAR AMINES

This invention relates to a process for the separation of dissimilar amines in a mixture thereof. More specifically, the invention is concerned with a process for separating a mixture of dissimilar amines into specific components by treating the mixture with a reactive carbonyl compound and an acid.

In many instances when various amines are formed by reaction processes, a mixture of various amines will be formed. For example, when preparing butylamine a mixture of n-butylamine, sec-butylamine and t-butylamine may be formed during the process. In some instances, it is desirable to obtain specific compounds and therefore it is necessary to separate or isolate the desired amine. This separation or isolation is necessary inasmuch as the various isomers may possess different properties and may be used for different reactions. For example, although n-butylamine and t-butylamine may be used in preparing insecticides or pharmaceuticals, n-butylamine may also find another use as an intermediate for emulsifying agents while t-butylamine may be used as an intermediate for rubber accelerators. Therefore, if the end use of one compound is for a specific purpose, it is necessary to separate out and isolate this isomer from other isomers which may be present. In a like manner, m-toluidine may be used in the manufacture of various organic chemicals while p-toluidine may be used as a test reagent for ligand, nitrite or phloroglucinol. In the event that one specific isomer is desired, these two compounds must then also be separated.

It is therefore an object of this invention to provide a process for the separation of dissimilar amine compounds.

A further object of this invention is to provide a process for the separation of dissimilar amines by treating said mixture in a manner hereinafter set forth in greater detail.

In one aspect, an embodiment of this invention resides in a process for the separation of dissimilar amines which comprises treating a mixture containing said dissimilar amines with a reactive carbonyl compound and an acid at reaction conditions, and recovering the separated amines.

A specific embodiment of this invention is found in a process for the separation of dissimilar amines which comprises a mixture of m-toluidine and p-toluidine with benzaldehyde and trifluoroacetic acid at a temperature in the range of from about ambient to about 150° C. and a pressure in the range of from about atmospheric to about 100 atmospheres, and recovering the separated m-toluidine and p-toluidine.

Other objects and embodiments will be found in the following further detailed description of the present invention.

As hereinbefore set forth the present invention is concerned with a process for the separation or isolation of dissimilar amines. Heretofore it was a general supposition that an amine exchange would only occur between amines that had a relatively large difference between their dissociation (pKa) values. As an example, it was felt that aromatic amines could be used to displace aliphatic amines. However, inasmuch as most alkyl amines possess pKa values that lie within a very narrow range, it was believed difficult to distinguish these amines on the basis of the relatively small pKa differences, thus rendering an attempt to separate or isolate the various amines a difficult step to accomplish. However, in contradistinction to this, it has now been discovered that isomeric amines can be separated by an exchange process even in the event that the difference in pKa values is relatively small. By utilizing the process of the present invention in which a mixture of amines which are dissimilar in nature by virtue of isomeric positions or by different carbon atom numbers, it is possible to effect a separation by treating with a reactive carbonyl compound and an acid. The separation will be effected by forming an imino derivative of the carbonyl compound with the amine which possesses the lower or lowest pKa and/or the amine which is the least hindered. Conversely, the acid salt of the amine which possesses the higher or highest pKa and which is the most hindered will be formed, thereby permitting a relatively simple separation.

Examples of amines which may be effectively separated according to the process of this invention will include alkyl amines containing from 1 to about 10 carbon atoms such as methylamine, ethylamine, n-propylamine, isopropylamine, n-butylamine, sec-butylamine, t-butylamine, the isomeric amylamines such as n-amylamine, sec-amylamine, isoamylamine, t-amylamine, 2-methylbutylamine, 3-aminopentane, 2-methyl-3-aminobutane, the corresponding isomeric hexyl, heptyl, octyl, nonyl and decyl amines, etc.; aryl amines such as phenylamine, naphthylamine, etc.; cycloalkyl amines such as cyclopentylamine, cyclohexylamine, 2-methylcyclopentylamine, 3-methylcyclopentylamine, 2-methylcyclohexylamine, 3-methylcyclohexylamine, 4-methylcyclohexylamine, 2-methylcycloheptylamine, 3-methylcycloheptylamine, 4-methylcycloheptylamine, etc., benzylamine, 2-aminoethylbenzene, 3-aminopropylbenzene, o-toluidine, m-toluidine, p-toluidine, 2,3-xylidine, 2,4-xylidine, 2,5-xylidine, 2,6-xylidine, 3,4-xylidine, 3,5-xylidine, etc. It is to be understood that the aforementioned amines are only representative of the class of compounds which may be separated and that the present invention is not necessarily limited thereto.

The aforementioned amines which are in admixture with one another are separated by treatment with a reactive carbonyl compound. In the preferred embodiment of the invention, the reactive carbonyl compound comprises benzaldehyde as well as substituted benzaldehydes including alkyl benzaldehydes such as o-methylbenzaldehyde, m-methylbenzaldehyde, p-methylbenzaldehyde, o-ethylbenzaldehyde, m-ethylbenzaldehyde, p-ethylbenzaldehyde, o-propylbenzaldehyde, m-propylbenzaldehyde, p-propylbenzaldehyde, o-butylbenzaldehyde, m-butylbenzaldehyde, p-butylbenzaldehyde, etc., o-methoxybenzaldehyde, m-methoxybenzaldehyde, p-methoxybenzaldehyde, o-ethoxybenzaldehyde, m-ethoxybenzaldehyde, p-ethoxybenzaldehyde, o-propoxybenzaldehyde, m-propoxybenzaldehyde, p-propoxybenzaldehyde, etc., o-chlorobenzaldehyde, m-chlorobenzaldehyde, p-chlorobenzaldehyde, o-bromobenzaldehyde, m-bromobenzaldehyde, p-bromobenzaldehyde, o-iodobenzaldehyde, m-iodobenzaldehyde, p-iodobenzaldehyde, etc. It is also contemplated within the scope of this invention that other compounds containing carbonyl radicals such as acetophenone, propiophenone, butyrophenone, etc., may also be employed. The acid component which is utilized to react with the amine containing the higher or highest pKa will include inorganic acids such as hydrochloric acid, hydrobromic acid, hydroiodic acid, etc., or organic acids such as methane sulfonic acid, ethane sulfonic acid, propane sulfonic acid, benzene sulfonic acid, toluene sulfonic acid, trifluoromethane sulfonic acid, trichloromethane sulfonic acid, trichloroacetic acid, trifluoroacetic acid, etc.

The treatment of the dissimilar amines with the reactive carbonyl compound and the acid is effected at reaction conditions which include temperatures in the range of from about ambient to about 150° C. or more and a pressure in the range of from about atmospheric to about 100 atmospheres. In the preferred embodiment of the invention, the reaction is effected at ambient temperatures and atmospheric pressures. However, if superatmospheric pressures are to be employed in the reaction, these pressures are afforded by the introduction of a substantially inert gas such as nitrogen, argon, helium, etc., into the reaction vessel capable of withstanding the superatmospheric pressure which is employed. The amount of pressure which is utilized will be that which is sufficient to maintain a major portion of the reactants in the liquid phase. In addition, the amount of reactive carbonyl compound and acid which is employed will be dependent upon the proportions of the amines which are present in the mixture. The amount of acid which is used will be that which is equivalent to the amount of amine of the highest pKa and/or greatest hindrance while the amount of carbonyl compound which is employed will be that which is equivalent to the amine of the lowest pKa and/or least hindrance. In the event that there are more than two dissimilar amines present in the reaction mixture the amount of acid and carbonyl compound will then be dependent upon whether it is desirable to separate the amine having the highest pKa or whether it is desirable to separate and isolate the amine possessing the lowest pKa. For example, if the desired product comprises the amine which possesses the highest pKa in a mixture containing three dissimilar amines, the amount of acid which is utilized will be that which is equivalent to the strongest base in the amine mixture while utilizing two equivalents of the carbonyl compound.

The process of the present invention may be effected in any suitable manner and may comprise either a batch or continuous type operation. For example, when a batch type operation is used a predetermined quantity of the amine mixture may be placed in a suitable apparatus following which the desired equivalent amount of acid and desired equivalent amount of reactive carbonyl compound are added. The mixture is then thoroughly admixed and allowed to react for a period of time which may range from about 0.5 up to about 16 hours or more in duration. Upon completion of the desired residence time the separated amines may be recovered as the salt of the acid and the carbonyl adduct of the reactive carbonyl compound. This separation may be facilitated by utilizing an inorganic acid in aqueous form, the salt of the acid being recovered in the aqueous layer of the reaction while the carbonyl adduct will be recovered in the organic phase of the reaction mixture. After recovery of the two compounds the desired amine may be recovered by decomposing the carbonyl adduct which is in the form of an imine by the addition of an acid while the acid salt may be subjected to neutralization with a basic compound such as sodium hydroxide, potassium hydroxide, sodium carbonate, potassium carbonate, etc., to recover the amine. While the aforementioned discussion has envisioned the use of ambient temperatures and atmospheric pressure in the reaction, it is also possible to effect the reaction by placing the amine mixture, the reactive carbonyl compound and the acid in a pressure resistant vessel such as an autoclave. Following this the autoclave may be pressured to the desired operating pressure by the introduction of a substantially inert gas of the type hereinbefore set forth following which the vessel is then heated to the desired operating temperature and maintained thereat for a predetermined period of time. Upon completion of the reaction time heating is discontinued, the vessel is allowed to return to room temperature and any excess pressure is discharged. The vessel is then opened and the reaction mixture is subjected to conventional means of separation of the type previously discussed.

It is also contemplated within the scope of this invention that the process may be effected in a continuous manner of operation. When utilizing this type of operation the starting materials comprising the amine mixture, the reactive carbonyl compound and the acid are continuously charged to a reaction vessel which is maintained at the proper operating conditions of temperature and pressure. After reaction in this vessel for a predetermined period of time the reactor effluent is continuously withdrawn and the reaction mixture is separated by conventional means into the amine salt and the imine adduct. After separation of the two products the desired amines may be recovered by treatment with acids and bases to form the desired product.

The following examples are given for purposes of illustrating the process of this invention. However, it is to be understood that these examples are given merely for purposes of illustration and that the present process is not necessarily limited thereto.

EXAMPLE I

A mixture comprising 1.06 grams (0.01 moles) of m-toluidine, 1.06 grams (0.01 moles) of p-toluidine, 1.07 grams (0.01 moles) of benzaldehyde and 1.14 grams (0.01 moles) of trifluoroacetic acid in methanol was admixed and allowed to stand for a period of 16 hours at ambient temperature and atmospheric pressure. At the end of this time the mixture was concentrated and extracted using carbonyl tetrachloride and water as the extractant material. The aqueous and organic phase was allowed to separate and the two layers were then separated using a separatory funnel. The organic phase was dried over anhydrous sodium sulfate and concentrated. Analysis of the imine was obtained by nuclear magnetic resonance and the organic phase was found to contain only m-toluidine.

The aqueous phase was made alkaline by the addition of a 5% sodium hydroxide solution and thereafter extracted with carbon tetrachloride. Following concentration of the product, analysis by means of nuclear magnetic resonance disclosed the presence of 100% of p-toluidine.

EXAMPLE II

In a manner similar to that set forth in Example I above, a mixture comprising 1.21 grams (0.01 moles) of 3,4-xylidine, 1.21 grams (0.01 moles) of 3,5-xylidine, 1.07 grams (0.01 moles) of benzaldehyde, and 1.14 grams (0.01 moles) of trifluoroacetic acid after thorough admixture was allowed to remain at ambient temperature and atmospheric pressure for a period of 16 hours. At the end of this time the mixture was concentrated and extracted with carbon tetrachloride and water. The organic phase and the aqueous phase were separated by means of a separatory funnel and after drying the organic phase over anhydrous sodium sulfate, it was subjected to a nuclear magnetic resonance analysis. This analysis determined that the organic phase contained only 3,5-xylidine. The aqueous phase was neutralized by the addition of a sufficient amount of a 5% sodium hydroxide solution and extracted with carbon tetrachloride. After concentrating the organic amine a nuclear magnetic resonance analysis determined that the amine consisted of only 3,4-xylidine.

EXAMPLE III

In this example, a mixture of 0.73 grams (0.01 moles) of t-butylamine, 0.73 grams (0.01 moles) of sec-butylamine, 1.07 grams (0.01 moles) of benzaldehyde, and 1.14 grams (0.01 moles) of trifluoroacetic acid in methanol was allowed to react for a period of 16 hours at ambient temperature and atmospheric pressure. At the end of this time the mixture was concentrated and extracted with carbon tetrachloride and water. The aqueous and organic layers were separated by means of a separatory funnel and the organic phase was dried over anhydrous sodium sulfate. After concentrating the organic phase said phase was subjected to a nuclear magnetic resonance analysis and it was determined that the organic phase contained only sec-butylamine.

The butylamine was too volatile in nature to be quantitated by neutralization and extraction, therefore the aqueous solution was concentrated to remove the water and the residual salts were analyzed by means of nuclear magnetic resonance in a deuterated dimethylsulfoxide medium, said analysis confirming the fact that this phase consisted only of the t-butylamine salt.

EXAMPLE IV

In this example a mixture consisting of 0.73 grams (0.01 moles) of isobutylamine, 0.73 grams (0.01 moles) of sec-butylamine, and 0.73 grams (0.01 moles) of t-butylamine in a medium comprising 2.14 grams (0.02 moles) of benzaldehyde and 1.14 grams (0.01 moles) of trifluoroacetic acid in methanol was subjected to a treatment similar in nature to that set forth in the above examples. After a reaction time of 16 hours at ambient temperature and atmospheric pressure, the mixture was extracted with carbon tetrachloride and water. After settling the organic phase and the aqueous phase were separated by means of a separatory funnel and the two phases were analyzed by means of nuclear magnetic resonance after treatment in a manner set forth above. It was found that the organic phase contained both isobutylamine and sec-butylamine while the aqueous phase contained only t-butylamine.

EXAMPLE V

In this example a mixture of equimolar proportions of n-amylamine and sec-amylamine may be separated by treating the mixture with equimolar proportions of benzaldehyde and hydrochloric acid. The treatment of the mixture may be effected in an autoclave at a reaction temperature of about 100° C. and a pressure of about 50 atmospheres, said pressure being provided for by the introduction of nitrogen into the autoclave. After allowing the reaction to proceed for a period of about 4 hours at this temperature and pressure, heating may be discontinued and the autoclave allowed to return to room temperature. After returning to room temperature the excess pressure may be discharged and the autoclave opened. The reaction mixture may be recovered from the autoclave and after settling the aqueous layer and the organic layer may be separated by means of a separatory funnel. After separation the organic layer will then be subjected to nuclear magnetic resonance analysis which will disclose the presence of n-amylamine while the aqueous layer after concentration and analysis in a like manner may disclose the presence of sec-amylamine.

I claim as my invention:

1. A process for the separation of dissimilar amines which comprises treating a mixture containing said dissimilar amines with a reactive carbonyl compound and an acid at reaction conditions, and recovering the separated amines.

2. The process as set forth in claim 1 in which said reaction conditions include a temperature in the range of from about ambient to about 150° C. and a pressure in the range of from about atmospheric to about 100 atmospheres.

3. The process as set forth in claim 1 in which said acid is hydrochloric acid.

4. The process as set forth in claim 1 in which said acid is trifluoroacetic acid.

5. The process as set forth in claim 1 in which said acid is methane sulfonic acid.

6. The process as set forth in claim 1 in which said reactive carbonyl compound is benzaldehyde.

7. The process as set forth in claim 1 in which said dissimilar amines are m-toluidine and p-toluidine.

8. The process as set forth in claim 1 in which said dissimilar amines are isobutylamine, sec-butylamine, and t-butylamine.

9. The process as set forth in claim 1 in which said dissimilar amines are 3,4-xylidine and 3,5-xylidine.

10. The process as set forth in claim 1 in which said dissimilar amines are n-amylamine and sec-amylamine.

* * * * *